United States Patent
Hirthe et al.

(10) Patent No.: US 6,850,865 B2
(45) Date of Patent: Feb. 1, 2005

(54) MONITORING AUTOMATIC TRANSMISSION FLUID CONDITION IN REAL TIME

(75) Inventors: Richard W. Hirthe, Milwaukee, WI (US); Steven R. Schachameyer, deceased, late of Mequon, WI (US); by Sher Schachameyer, legal representative, Mequon, WI (US); Lian Q. Zou, Glendale, WI (US); Victor E. Shtaida, Franklin, WI (US)

(73) Assignee: Eaton Corporation, Cleveland, OH (US)

( * ) Notice: Subject to any disclaimer, the term of this patent is extended or adjusted under 35 U.S.C. 154(b) by 103 days.

(21) Appl. No.: 10/319,323

(22) Filed: Dec. 13, 2002

(65) Prior Publication Data

US 2004/0117147 A1 Jun. 17, 2004

(51) Int. Cl.$^7$ ................................. G06F 17/18
(52) U.S. Cl. ................ 702/181; 702/22; 702/50; 324/439; 324/444; 324/698
(58) Field of Search ................. 702/181, 130, 702/22, 34, 50; 324/441, 439, 450, 698, 724, 446, 444

(56) References Cited

U.S. PATENT DOCUMENTS

| | | | | |
|---|---|---|---|---|
| 5,274,335 A | * | 12/1993 | Wang et al. | 324/689 |
| 5,382,942 A | * | 1/1995 | Raffa et al. | 340/457.4 |
| 6,278,281 B1 | | 8/2001 | Bauer et al. | 324/441 |
| 6,377,052 B1 | | 4/2002 | McGinnis et al. | 324/446 |
| 6,380,746 B1 | | 4/2002 | Polczynski et al. | 324/446 |
| 6,433,560 B1 | | 8/2002 | Hansen et al. | 324/668 |

OTHER PUBLICATIONS

Jo Ameye, Rapid and cost–effective determination of the remaining useful life (RUL) of industrial lubricants by voltammetric techniques (Oct. 24–26, 2000).*

* cited by examiner

*Primary Examiner*—John Barlow
*Assistant Examiner*—Hien Vo
(74) *Attorney, Agent, or Firm*—Roger A. Johnston

(57) ABSTRACT

A tubular probe having annularly spaced electrodes is immersed in ATF and sequentially excited with an alternating voltage at a relatively high and low frequency. The current is measured at both frequencies and the difference in impedance computed; and, the differential impedance is corrected for temperature and the corresponding value of one of TAN per ASTM D-669, Delta Oxidation per ASTME-168 ($\Delta OX$) and HPDSC induction time per ASTM D-5483 (MIN) determined from a lookup table of values of TAN, $\Delta OX$ and MIN versus impedance differential for known fluid conditions. The remaining useful life (RUL) may then be computed from determined present value of TAN, $\Delta OX$ or MIN. When the temperature corrected impedance difference $\Delta Z_{TC}$ reaches $6.5 \times 10^5$ Ohms, the ATF is considered to have reached the end of its useful life.

10 Claims, 12 Drawing Sheets

MONITORING AUTOMATIC TRANSMISSION FLUID CONDITION IN REAL TIME

BACKGROUND OF THE INVENTION

The present invention relates to fluid condition monitoring utilizing a sensor providing an electrical signal indicating in real time the chemical condition of the fluid to be monitored. Sensors of this type are known to employ impedance spectroscopy techniques; and, an example of such a sensor is that shown and described in U.S. Pat. No. 6,278,281 Bauer, et al granted Aug. 21, 2001 in which a pair of spaced electrodes are sequentially excited at a relatively low frequency for determining the electrochemical interaction at the electrode surface and at a relatively high frequency for determining the bulk impedance of the fluid. The current is measured at both excitation frequencies and the impedance computed for each current measurement and the impedance differential computed which enables determining the fluid condition by a comparison of the computed impedance differential with that determined for known conditions of the fluid as determined by chemical analysis.

It has been proposed to use such devices for monitoring fluid condition in power transmissions and for real time monitoring of lubricating oil in combustion engines. A further example of such a sensor application for engines is that shown and described in U.S. Pat. No. 6,377,052, McGinnis, et al granted Apr. 23, 2002 in which the spaced electrodes are spirally wound on a dipstick for insertion into the engine crankcase.

Devices of the aforesaid type employing impedance spectroscopy may utilize the electrode arrangements of the type employing interdigitated planar arrays of electrodes or the aforementioned spiral arrangement or concentric radially spaced tubular electrodes such as for example those taught in U.S. Pat. No. 6,433,560 issued to Hansen et al. and granted Aug. 13, 2002.

The aforesaid Bauer, et al. patent describes in FIG. 15 thereof the impedance determined at the aforesaid high and low frequencies for automatic transmission fluid in the new condition and after a limited number of vehicle miles in service.

However, since actual vehicle service conditions depend upon the type of vehicle operation and the loading and environment during such operation, it has long been desired to provide a sensor which can provide over the service life of the vehicle a real time indication of the fluid condition based upon the actual chemical characteristics of the fluid and to indicate the amount or percentage of estimated remaining useful life (RUL) based upon the current condition of the fluid.

BRIEF SUMMARY OF THE INVENTION

The present invention provides a technique for generating a continuously varying electrical signal in real time indicative of the chemical condition of the fluid being monitored and employs algorithms based upon sensor readings in samples of fluid of known chemical conditions to provide a database for comparison with the real time electrical signal for providing an indication of the remaining useful life (RUL) based upon the current condition of the fluid.

The present invention provides algorithms for determining the RUL of automatic transmission fluid, particularly fluid of the type comprising solvent dewaxed paraffinic oil in real time based upon differential impedance techniques. The present invention employs a pair of spaced electrodes configured preferably as concentrically disposed radially spaced annular electrodes for improved dispersion of the fluid over the electrode surfaces. The present invention utilizes any of three parameters derived from chemical analysis of the fluid, namely total acid number (TAN) per ASTM D-664, delta Oxidation per ASTM e-168 (ΔOX) and HPDSC induction time per ASTM D-5483 (MIN).

DETAILED DESCRIPTION OF THE INVENTION

Figure 1:
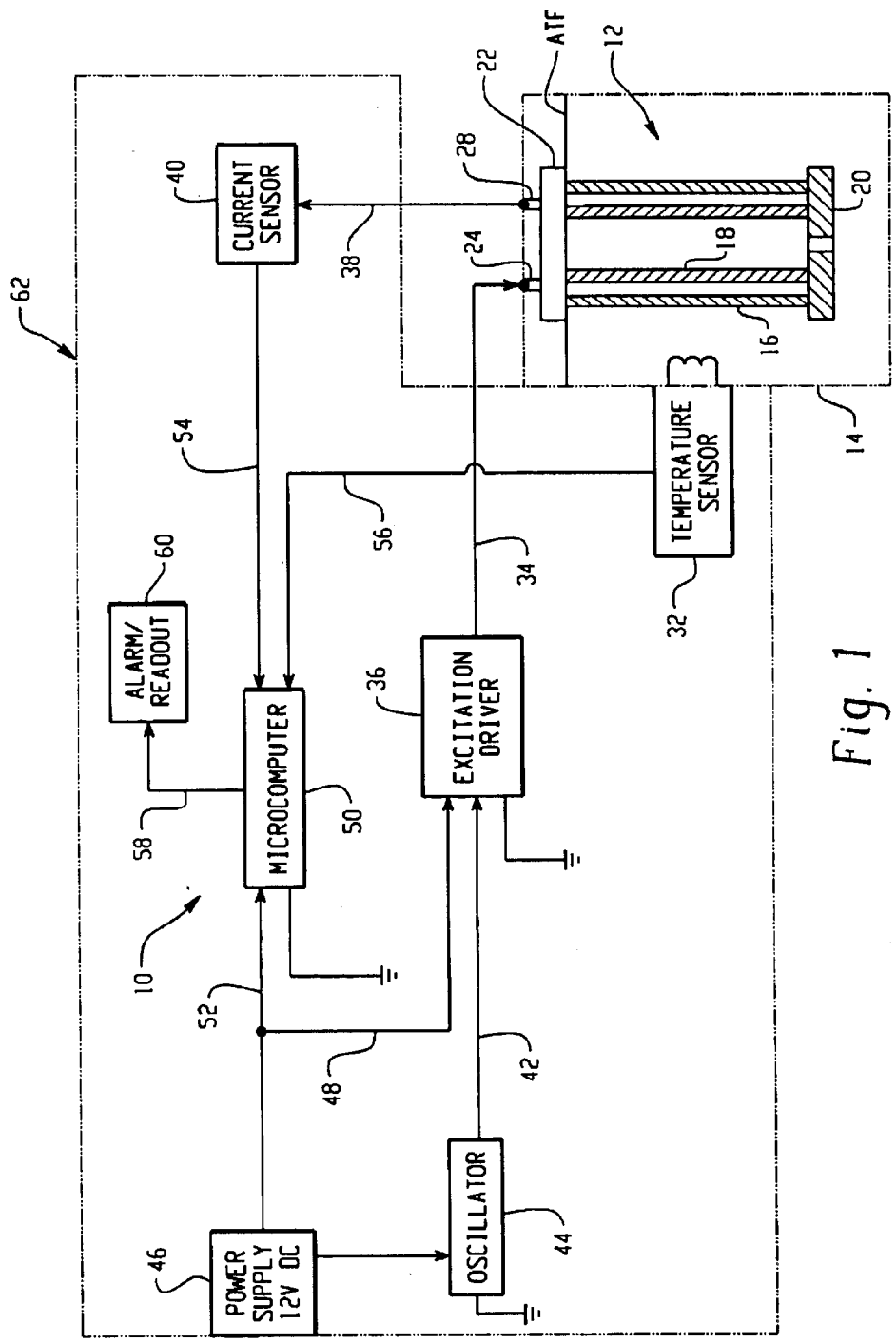
FIG. 1 is a pictorial block diagram of the sensor of the present invention deployed in a fluid filled transmission casing.
Figure 5:
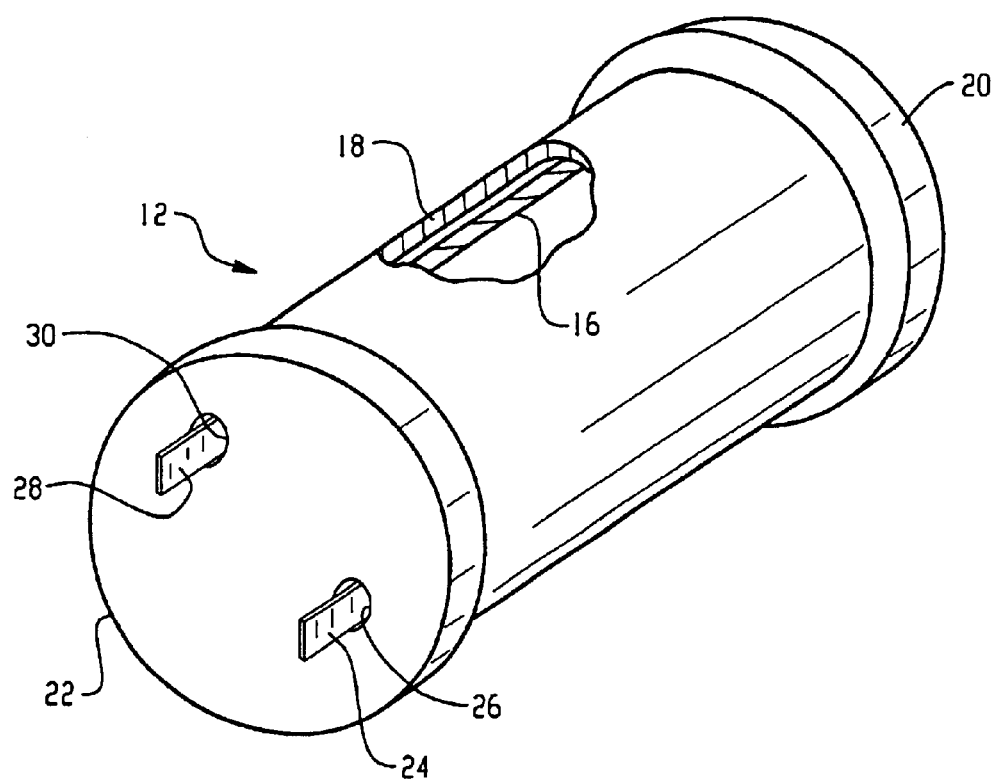
FIG. 5 is a perspective view of the probe of the present invention.

Referring to FIGS. 1 and 5, the sensor of the present invention is indicated generally at 10 and includes a probe assembly indicated generally at 12 immersed in fluid denoted ATF contained in an automatic transmission housing or casing 14. The present invention is particularly useable with ATF of the type having solvent dewaxed heavy paraffinic oil as the essential ingredient The sensor 12 may comprise any of those known in the art, as for example, an interdigitated planar array or spirally configured electrode pair; however, in the presently preferred practice the probe 12 comprises a pair of concentrically disposed radially spaced tubular or annular electrodes 16, 18 retained in closely spaced concentric or nested arrangement by end caps 20, 22. Inner tubular electrode 16 has a connector terminal 24 extending axially therefrom and outwardly through a clearance slot 26 formed in header 22; and, similarly outer electrode 18 has a connector terminal 28 extending outwardly through slot 30 formed in cap 22.

A temperature sensor, which may comprise a thermistor device, indicated by reference numeral 32 is disposed such that the sensing element thereof is exposed to the ATF within the casing 14.

The inner electrode terminal 24 is connected along line 34 to receive an excitation signal from driver 36. The connector terminal 28 is connected along line 36 to a current sensor 40.

In the presently preferred practice of the invention, the probe 12 has the concentric electrodes 16, 18 spaced radially a distance of about 0.15 mm for an inner electrode 18 having a diameter of about 6 mm and a length of about 38 mm. It will be understood however that other diameters and lengths may be employed to provide about the same surface area exposed between the electrodes. In the presently preferred practice the electrodes 16, 18 are formed of stainless steel; however, other electrode materials may be employed which are compatible with the ATF. In the present practice, the invention has been found particularly suitable for use with ATF comprising solvent dewaxed heavy paraffinic oil but the invention may be employed with other types of ATF.

Referring again to FIG. 1, the excitation driver 36 receives an input along line 42 from an oscillator 44 which is powered by an on-board vehicle supply such as the 12 Volt DC supply 46 which also supplies the excitation driver 36 along line 48. A microcomputer 50 is powered by the power supply 46 along line 52; and, the microcomputer receives an input along line 54 from the current sensor 40 and a temperature input along line 56 from sensor 32 and provides an output along line 58 to an alarm or readout device 60.

In the present practice of the invention, the oscillator 44 provides a low frequency alternating voltage of a frequency not greater than about 0.1 Hertz (100 milliHertz) and a relatively high frequency alternating voltage at a frequency not less than about 7.5 Hertz.

The microcomputer 50 is programmed with lookup tables based upon data taken from laboratory chemical aging of the ATF and determining the differential impedance at successive intervals. The fluid samples were tested to determine any one of three known test parameters, namely Total Acid Number per ASTM D-664 (TAN), delta Oxidation per ASTM E168 ($\Delta$OX) and HPDSC induction time per ASTM D-5483 (MIN). The data is then plotted for each of the parameters and curves drawn therebetween as displayed respectively in FIGS. 6 through 8. The graphs include data points taken for ATF stressed by laboratory oxidation aging tests, such as an Aluminum Beaker Oxidation Test (ABOT) per Southwest Research Institute, San Antonio, Tex. procedure BJ110-4 and some ATF fluid drained from vehicles in actual road service. It will be noted from FIGS. 6 through 8 that the linear approximations may be made for the data; and, algorithms for the slope used to calculate the respective chemical parameter for valves of $\Delta Z_{TC}$ are indicated on the graphs.

Figure 2A:
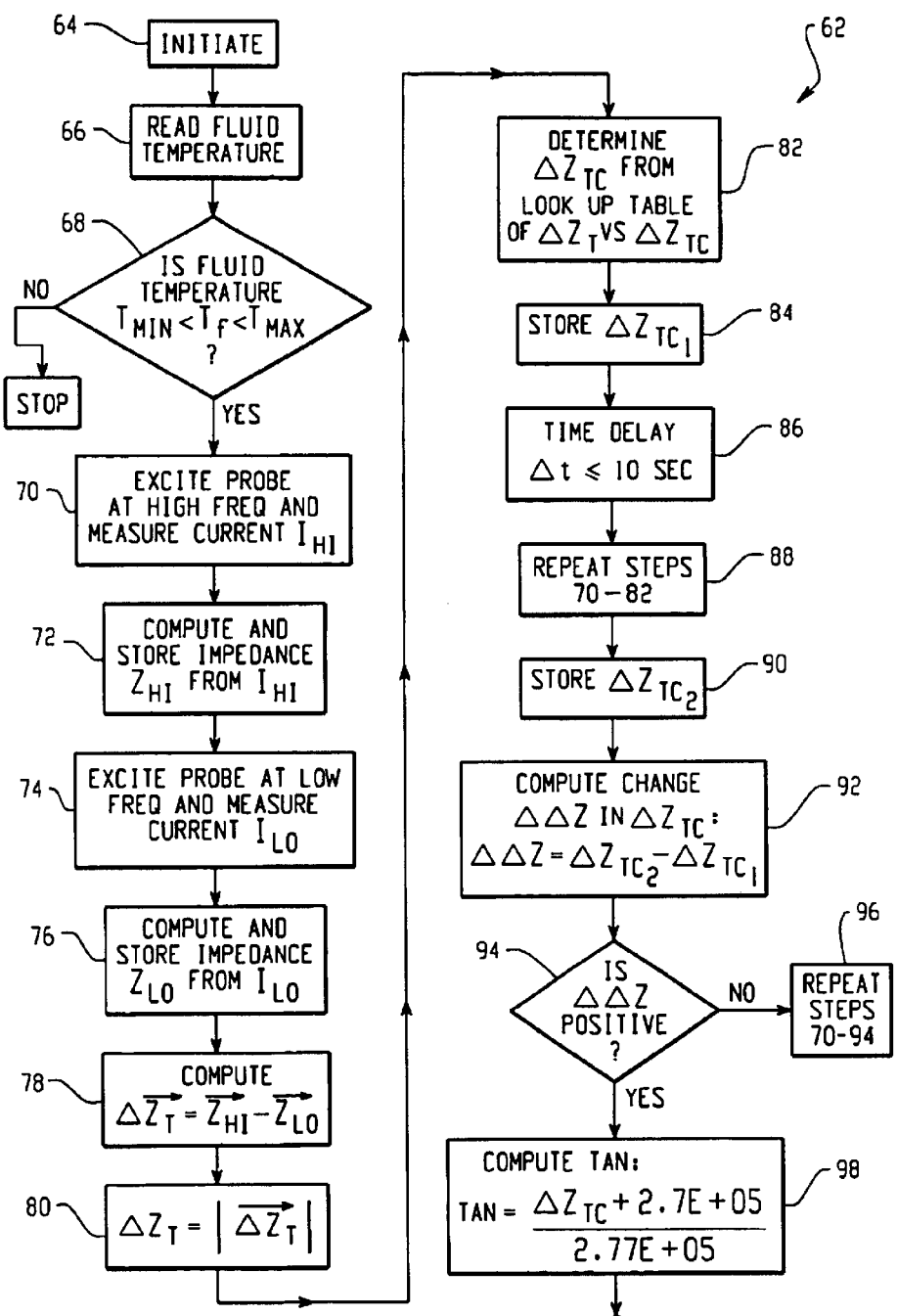
FIGS. 2A and 2B are a block flow diagram of the system operation for determining RUL based on TAN.
Figure 2B:
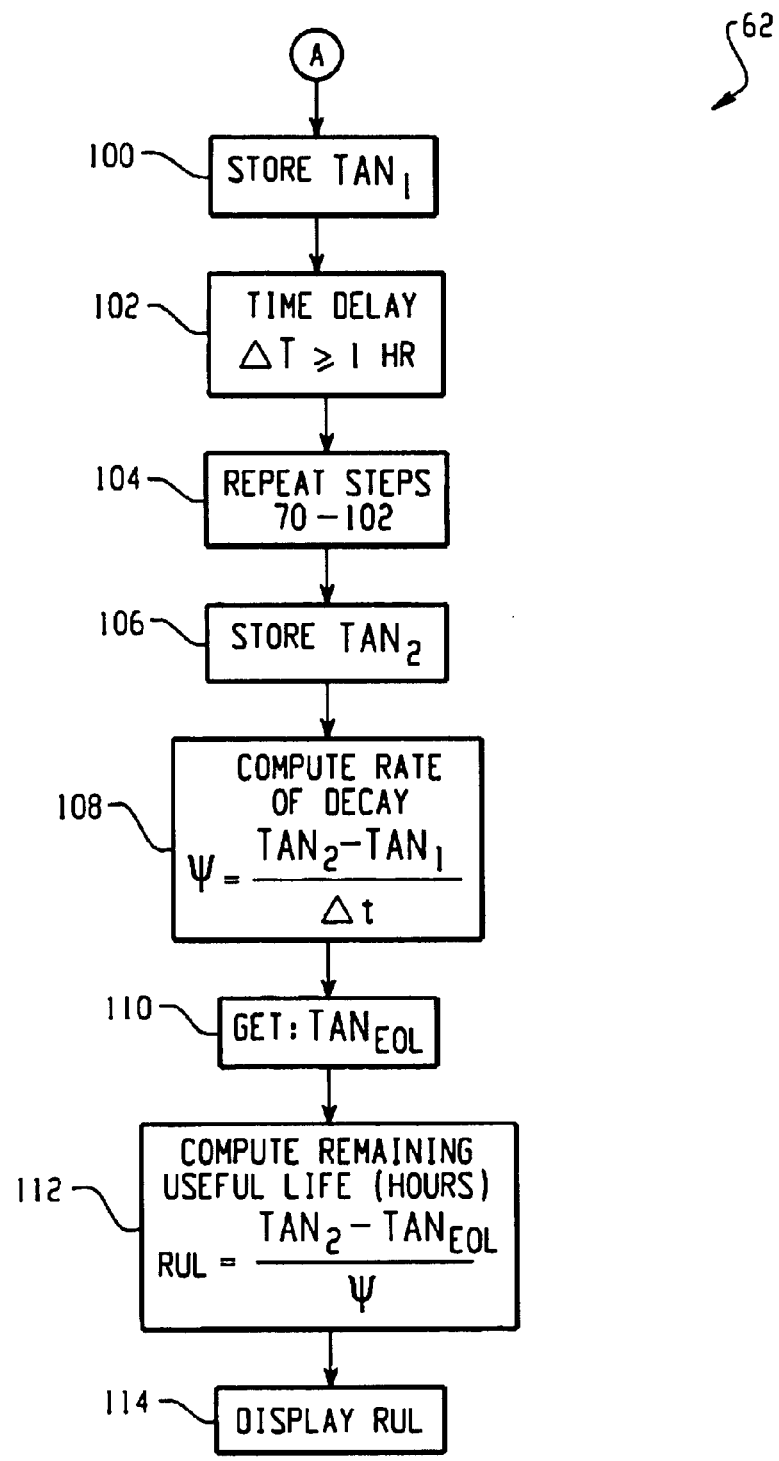

Referring to FIG. 2, the operation of the system circuitry is denoted generally by reference numeral 62; and, upon user initiation at step 64 the system proceeds to step 68. At step 68 the system inquires as to whether the fluid temperature $T_f$ is within desired limits $T_{MIN}$, $T_{MAX}$; and, if the answer is negative the system proceeds to abort or Stop. However, if the determination at step 68 is affirmative, the system proceeds to step 70 and excites the probe 32 with an alternating voltage at a relatively high frequency and measures the current $I_{HI}$. The system then proceeds to step 72 and computes and stores the impedance $Z_{HI}$ from the measured current $I_{HI}$.

The system then excites the probe 32 with a relatively low frequency alternating voltage and measures the current $I_{LO}$ and proceeds to step 76 and computes and stores the impedance $Z_{LO}$ from the measured current $I_{LO}$.

Figure 9:
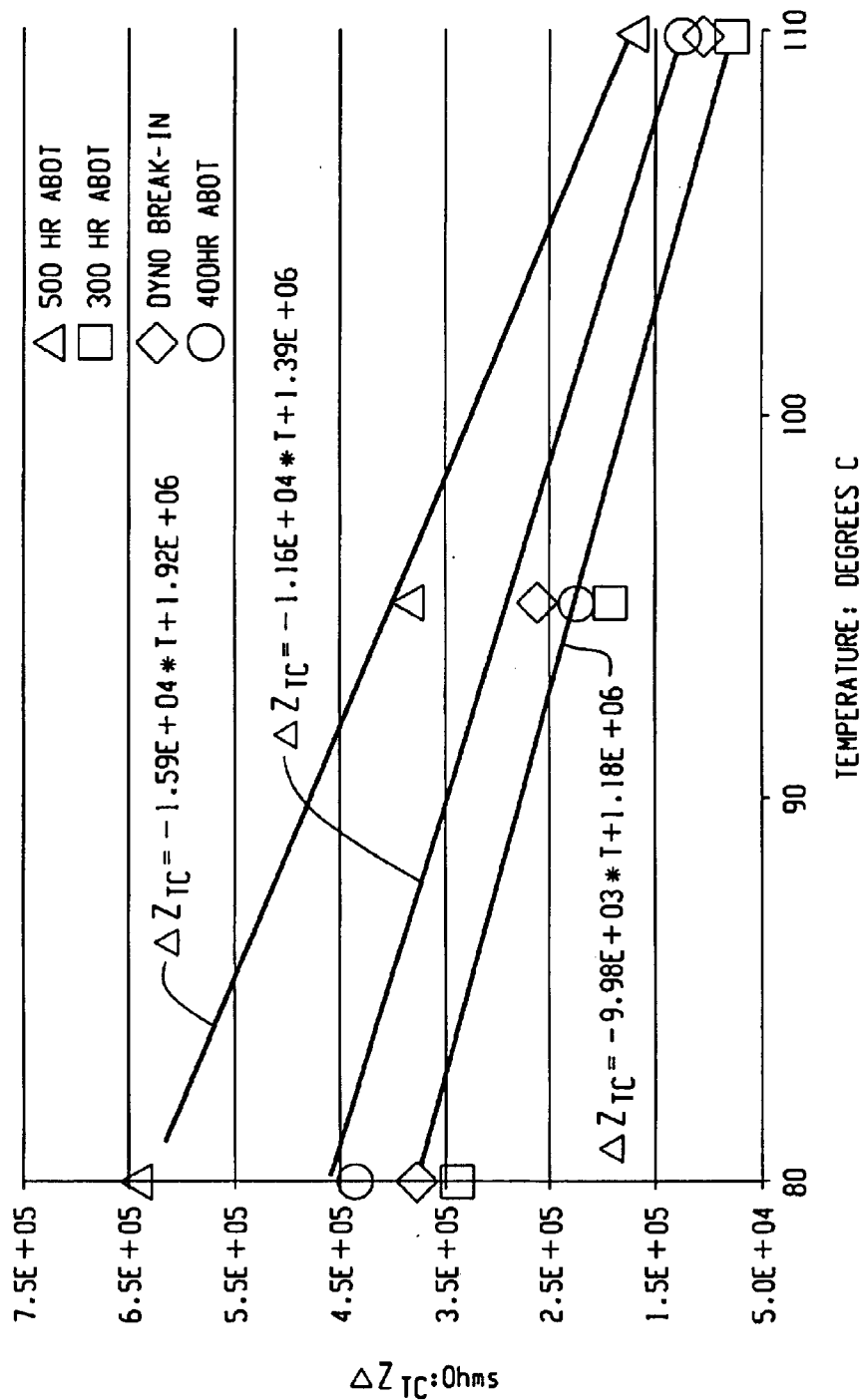

The system then proceeds to step 78 and computes the vector $\Delta \vec{Z}_T$ by subtracting $\vec{Z}_{LO}$ from $\vec{Z}_{HI}$ yielding the vector result $\Delta \vec{Z}_T$. The system then proceeds to step 80 and computes the absolute value of $\Delta Z_T$ and proceeds to step 82 and determines $\Delta Z_{TC}$ the temperature compensated impedance differential from a lookup table of values of $\Delta Z_{TC}$ versus temperature, which table is compiled by taking data points from a temperature correction curve. Typical curves for such temperature compensation are shown in FIG. 9.

It will be seen that a family of three plots; namely on upper graph:

$$\Delta Z_{TC} = -1.59E+04 * T + 1.92E+06,$$

a lower graph:

$$\Delta Z_{TC} = -9.98E+03 * T + 1.18E+06$$

and a middle graph:

$$\Delta Z_{TC} = -1.16E+04 * T + 1.39E+06$$

plotted by interpolating between the upper and lower graph are presented in FIG. 9. It will be noted that the shapes and intercepts of the three graphs are similar; and, thus provide a region from which $\Delta Z_{TC}$ may be computed.

The system then proceeds to store the value determined at step 82 as $\Delta Z_{TC_1}$ at step 84; and, after a suitable time delay of not more than about 10 seconds at step 86 the system proceeds to step 88 and repeats steps 70 through 82 and stores the result as $\Delta Z_{TC_2}$ at step 90.

The system then proceeds to step 92, computes the change in $\Delta Z$ denoted $\Delta\Delta Z$ by subtracting $\Delta Z_{TC_1}$ from $\Delta Z_{TC_2}$ and proceeds to step 94 and inquires as to whether $\Delta\Delta Z$ is positive.

Figure 6:
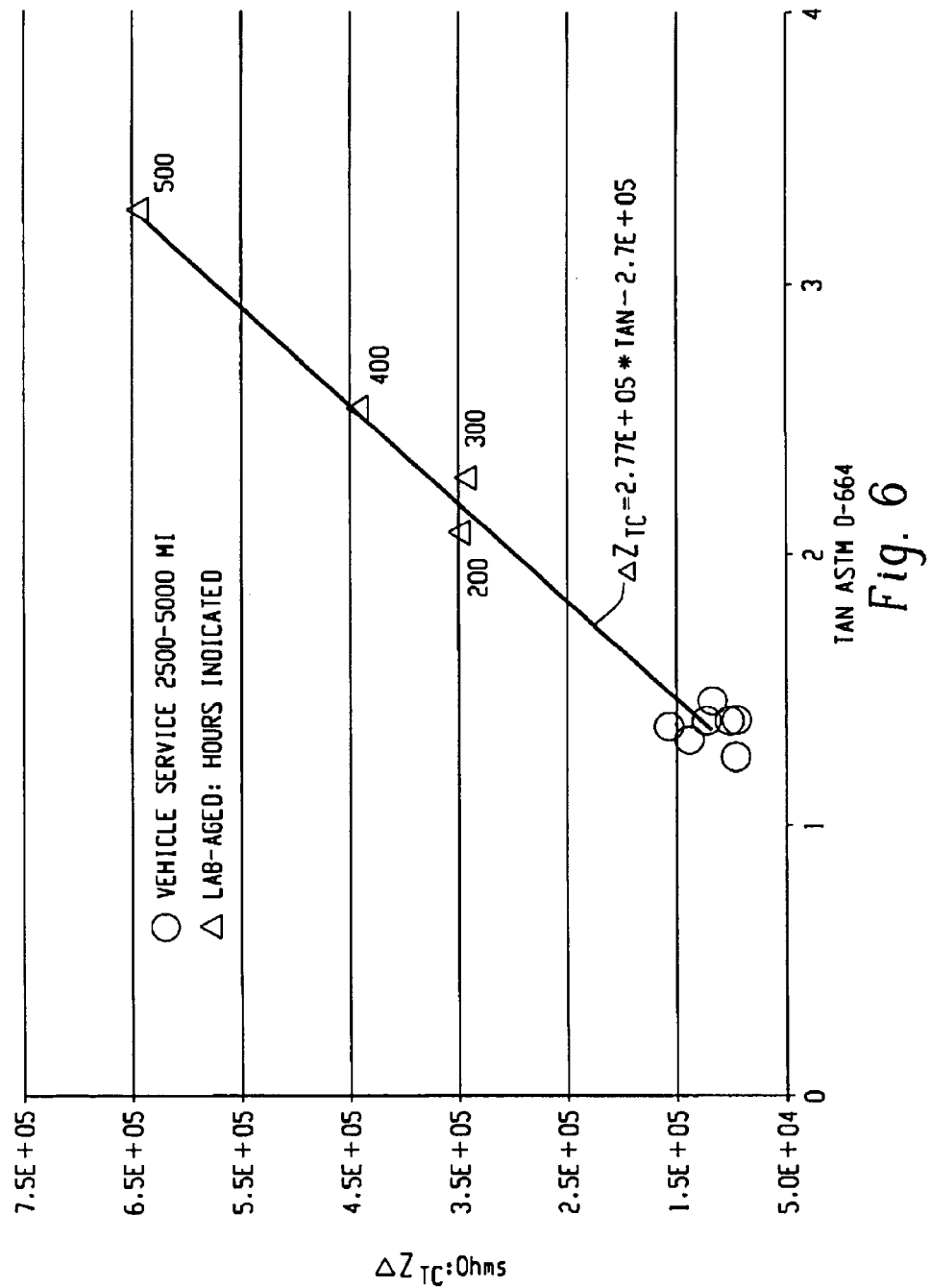
FIG. 6 is a graph plotting differential impedance values as a function of TAN.

If the determination at step 94 is affirmative the system proceeds to step 98 and computes TAN from a lookup table of values of TAN versus $\Delta Z_{TC}$ based upon the algorithm from FIG. 6:

$$\Delta Z_{TC} = 2.77E+05 * TAN - 2.7E+05$$

If however, the determination at step 94 is negative, the system proceeds to step 96 and repeats steps 70 through 94.

After completion of any of step 98, the system proceeds to step 100 and stores the determined value as $TAN_1$ and proceeds to step 102 for a time delay $\Delta T$ of not less than about one hour. The system then proceeds to step 104 and repeats steps 70 through 102 and stores the result as $TAN_2$ at step 106. The system then proceeds to step 108 and computes the rate of decay $\psi$ by subtracting $TAN_1$ from $TAN_2$ and dividing the differential by $\Delta T$. The system then proceeds to step 110 and recalls a stored value $TAN_{EOL}$ and then proceeds to step 112 and computes the remaining useful life in hours (RUL) by subtracting $TAN_{EOL}$ from $TAN_2$ and dividing the differential by $\psi$. The system then displays the computed value of RUL at step 114.

Figure 3A:
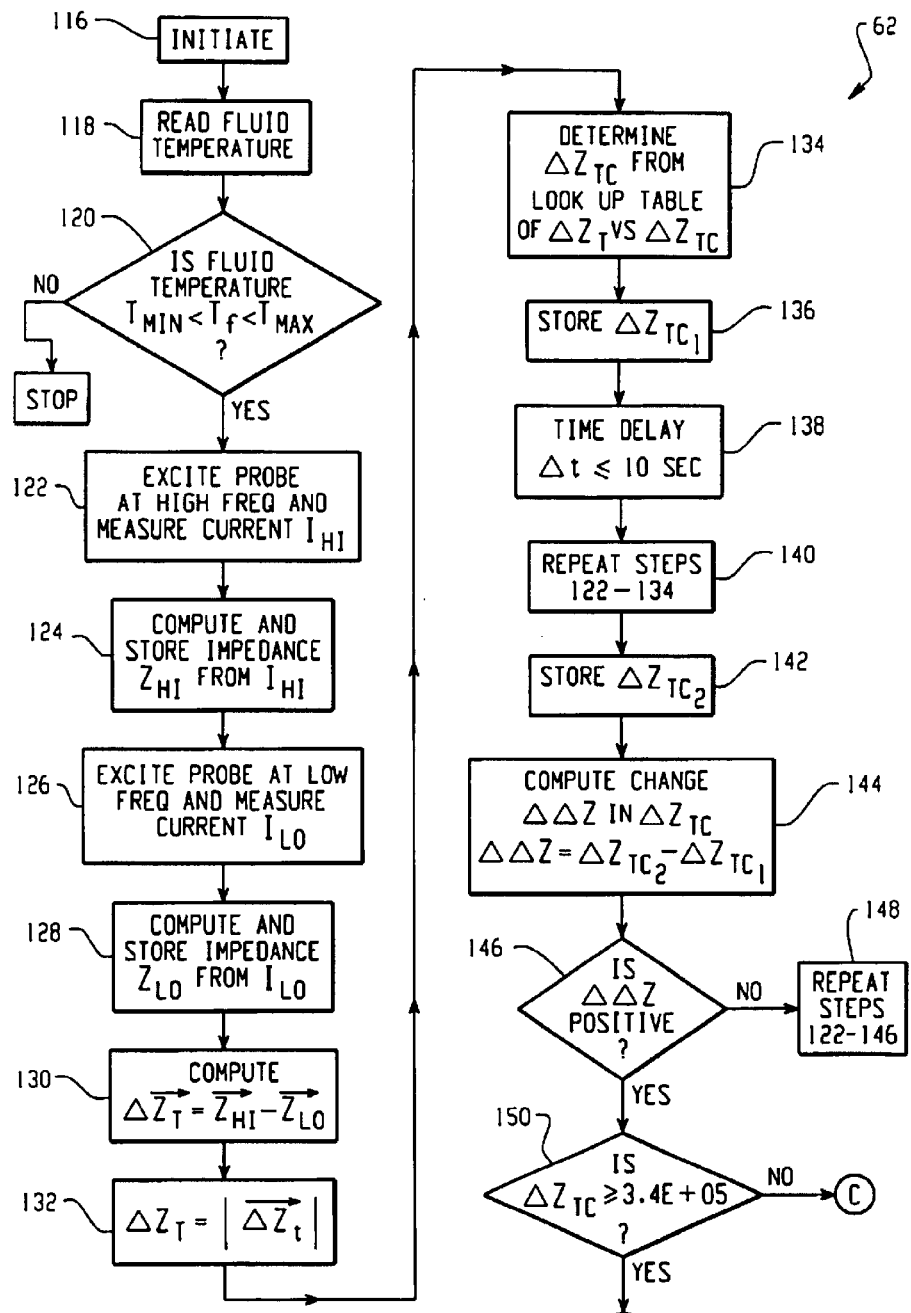
FIGS. 3A and 3B are a flow diagram similar to FIG. 2 for MIN.
Figure 3B:
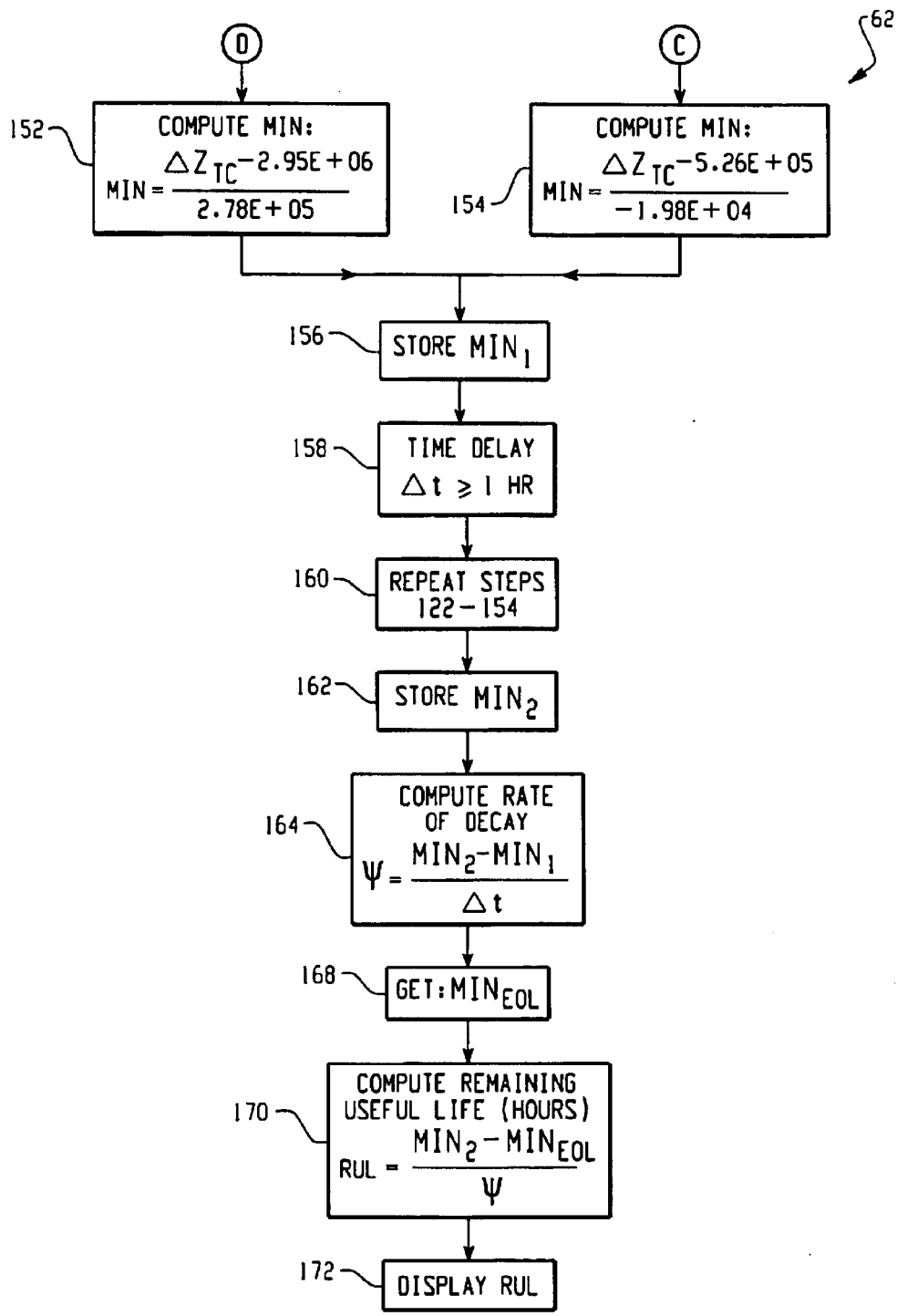

Referring to FIG. 3, the flow diagram for determining RUL from the parameter HPDSC induction time per ASTM D-5483 (MIN) is shown wherein the system, upon initiation at step 116 proceeds to read the fluid temperature at step 118 from the sensor 32. The system then proceeds to step 120 and asks whether the temperature read at $T_f$ read at step 118 is between the limits $T_{MIN}$, $T_{MAX}$; and, if the determination is negative the system proceeds to abort or Stop. However, if the determination at step 120 is affirmative the system proceeds to step 122 and excites the probe at the relatively high frequency alternating voltage and measures the current $I_{HI}$. The system then proceeds to step 124, computes and stores the impedance $Z_{HI}$ computed from the current measured at step 122.

The system then proceeds to step 126 and excites the probe at the relatively low frequency alternating voltage and measures the current $I_{LO}$. The system then proceeds to step 128 and computes and stores the impedance $Z_{LO}$ from the current measured in step 126.

The system then proceeds to step 130, computes the vector difference $\Delta \vec{Z}_t$ by subtracting $\vec{Z}_{LO}$ from $\vec{Z}_{HI}$ and proceeds to step 132 and determines the absolute value $\Delta Z_T$.

The system then proceeds to step 134 and determines $\Delta Z_{TC}$ from a lookup table of $\Delta Z_T$ versus Temperature which lookup table is determined from data points taken from curves such as those shown in FIG. 9 which identify the change in the differential impedance with temperature for samples of fluid of known condition. The procedure is the same as for step 82.

The system then proceeds to step 136 and stores the value $\Delta Z_{TC_1}$ computed at step 134 and proceeds to step 138 for a time delay of not more than about ten seconds. The system then proceeds to step 140 and repeats steps 122 through 134 and stores the computed value $\Delta Z_{TC_2}$ at step 142.

The system then proceeds to compute the change in $\Delta Z_{TC}$ denoted $\Delta\Delta Z$ by subtracting $\Delta Z_{TC_1}$ from $\Delta Z_{TC_2}$. The system then proceeds to step 146 and asks whether $\Delta\Delta Z$ is positive; and, if the answer is affirmative the system proceeds to step 148 and repeats steps 122 through 146. However, if the determination at step 146 is negative, the system proceeds to step 150 and asks whether $\Delta Z_{TC}$ is equal to or greater than 3.4E+05. If the query in step 150 is answered in the affirmative, the system proceeds to step 152 and determines MIN from a lookup table of values of MIN versus $\Delta Z_{TC}$ compiled from the graph of FIG. 8 using the algorithm:

$$\Delta Z_{TC} = -2.78E+05 * MIN + 2.95E+06.$$

Figure 8:
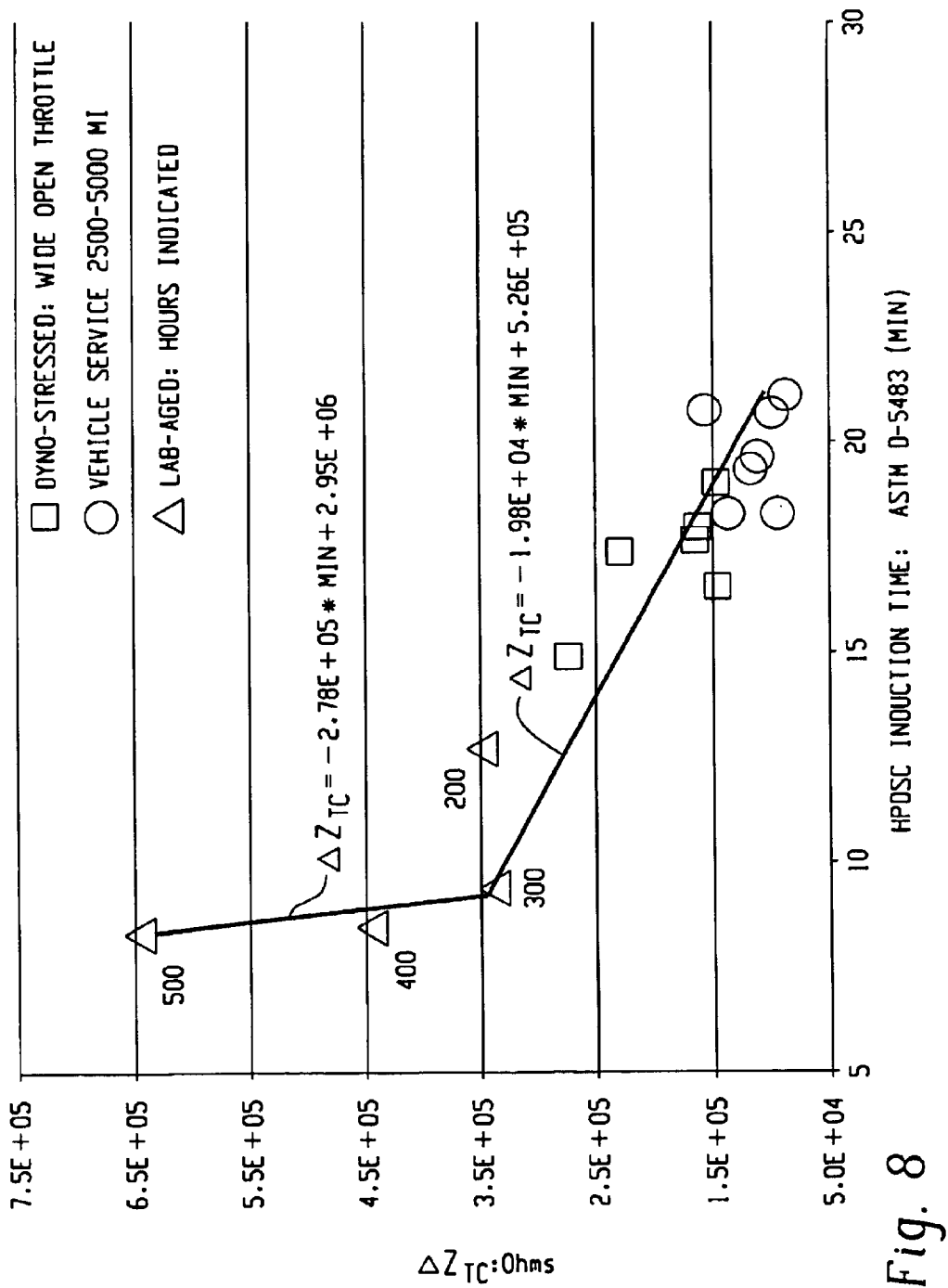
FIG. 8 is a graph plotting values of differential impedance as a function of MIN and, FIG. 9 is a graph of changes with temperature of values of ΔZ.

However, if the determination at step 150 is negative the system proceeds to step 154 and determines MIN from a lookup table of values of $\Delta Z_{TC}$ versus MIN compiled from the graph of FIG. 8 using the algorithm:

$$\Delta Z_{TC} = -1.98E+04 * MIN + 5.26E+05.$$

Upon completion of one of the steps 152 or 154 the system proceeds to step 156 and stores the determined value of MIN as $MIN_1$ and proceeds to step 158 for a time delay $\Delta T$ of not less than about one hour and then proceeds to step 160 and repeats steps 122 through 154. The value of MIN determined at step 160 is then stored as $MIN_2$ at step 162 and the system proceeds to step 164 and computed the rate of decay by $\psi$ determined by subtracting $MIN_1$ from $MIN_2$ and dividing the differential by $\Delta T$.

The system then proceeds to step 168 to get a stored value of $MIN_{EOL}$ and proceeds to step 170 and computed the remaining useful life RUL by subtracting $MIN_{EOL}$ from $MIN_2$ and dividing the differential by $\psi$ as determined in step 164. The system then proceeds to display the computed value of RUL at step 172.

Figure 4A:
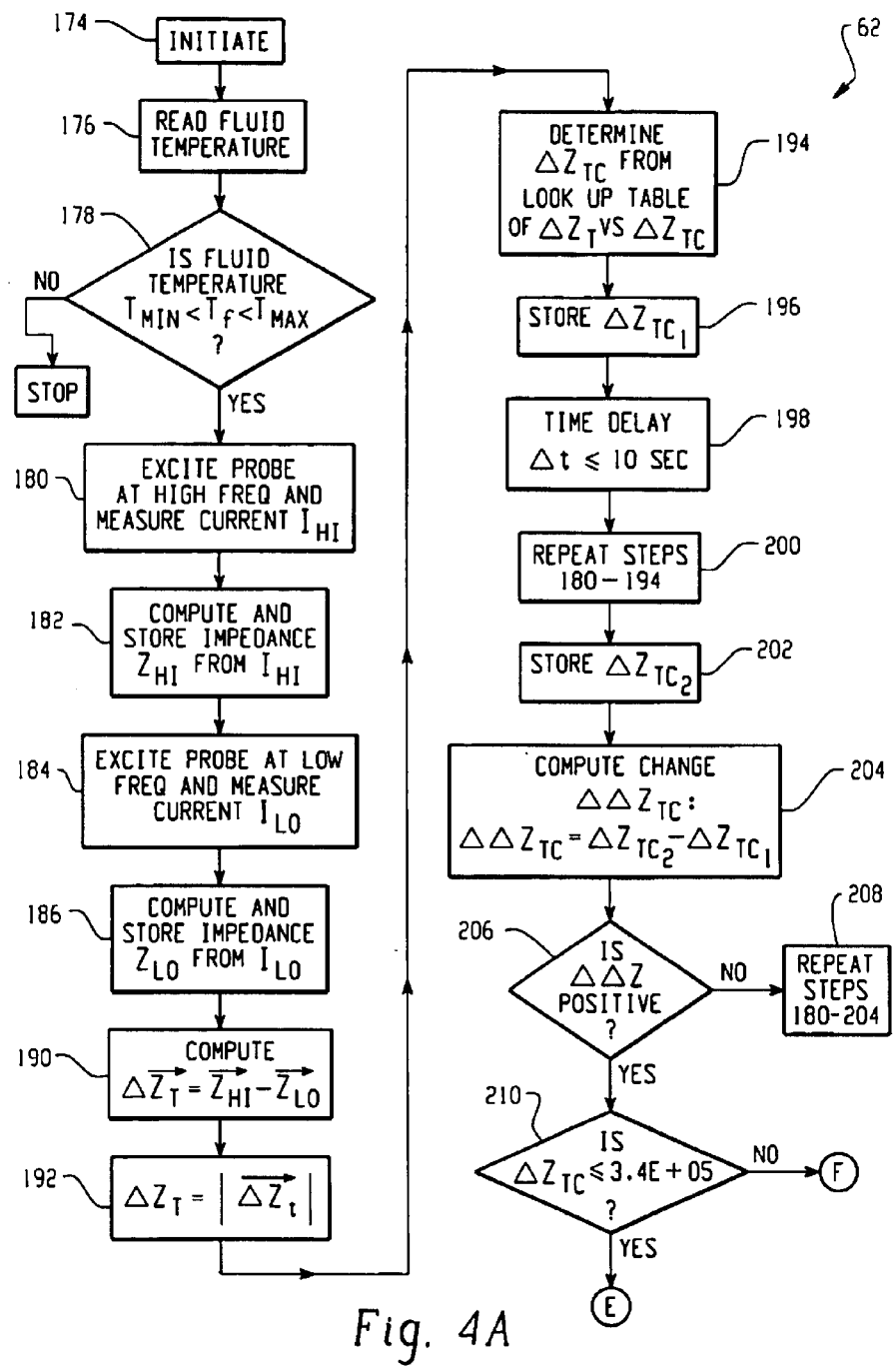
FIGS. 4A and 4B are a block diagram similar to FIG. 2 for ΔOX.
Figure 4B:
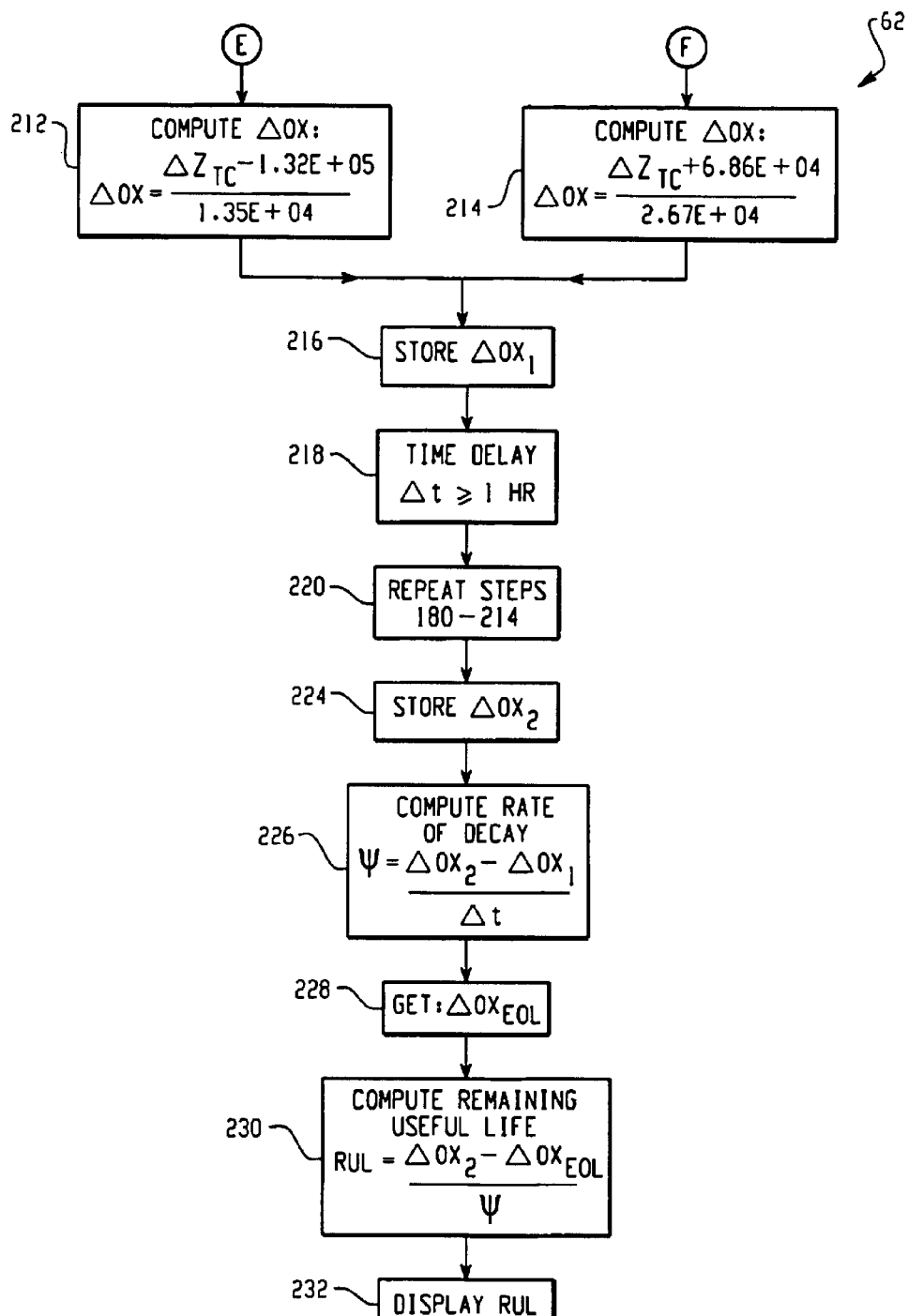

Referring to FIG. 4, the flow diagram for determining RUL from the parameter Delta Oxidation per ASTM E-168 ($\Delta OX$) is shown wherein the system, upon user initiation at step 174, proceeds to read the fluid temperature at step 176 and then proceeds to step 178 to determine if temperature $T_f$ is within the limits $T_{MIN}$, $T_{MAX}$. If the determination at step 178 is negative the system aborts or proceeds to Stop. However if the determination at step 178 is affirmative, the system proceeds to step 180 to excite the probe 32 with a relatively high frequency alternating voltage and measures the resultant current $I_{HI}$. The system then proceeds to step 182, computes the impedance $Z_{HI}$ from the measured current and stores the computed value. The system then proceeds to step 184 and excites the probe 12 with a relatively low frequency alternating voltage and measures the resultant current $I_{LO}$ and proceeds to step 186 and computes and stores the impedance $Z_{LO}$ from the measured current $I_{LO}$.

The system then proceeds to step 190 and computes the impedance vector differential $\Delta\vec{Z}_t$ by subtracting $\vec{Z}_{LO}$ from $\vec{Z}_{HI}$ and then determines the absolute value of the computed differential $\Delta Z_T$ at step 192.

The system then proceeds to step 194 and determines the temperature compensated value $\Delta Z_{TC}$, compiled from data points taken from curves such as shown FIG. 9 from the lookup table of values of $\Delta Z_{TC}$ versus temperature and, the system then proceeds to step 196 and stores the computed value as $\Delta Z_{TC_1}$.

The system then proceeds to step 198 and provides a time delay of not more than about 10 seconds and then proceeds to step 200 and repeats steps 180 through 194 and stores the computed value as $\Delta Z_{TC_2}$ at step 202.

The system then computes the change $\Delta\Delta Z$ in the differential impedance $\Delta Z$ by subtracting $\Delta Z_{TC_1}$ from $\Delta Z_{TC_2}$ at step 204 and proceeds to step 206 and asks the question whether $\Delta\Delta Z$ is positive. If the answer to the query in step 206 is negative, the system proceeds to step 208 and repeats steps 180 through 204. If the query in step 206 is answered in the affirmative, the system proceeds to step 210 and asks whether $\Delta Z_{TC}$ is equal to or less than 3.40E+05. If the determination in step 210 is affirmative, the system proceeds to step 212 and determines from a lookup table the values of $\Delta OX$ versus $\Delta Z_{TC}$ compiled from the graph of FIG. 7 using the algorithm:

$$\Delta Z_{TC} = 1.35E+04 * \Delta OX + 1.32E+05.$$

Figure 7:
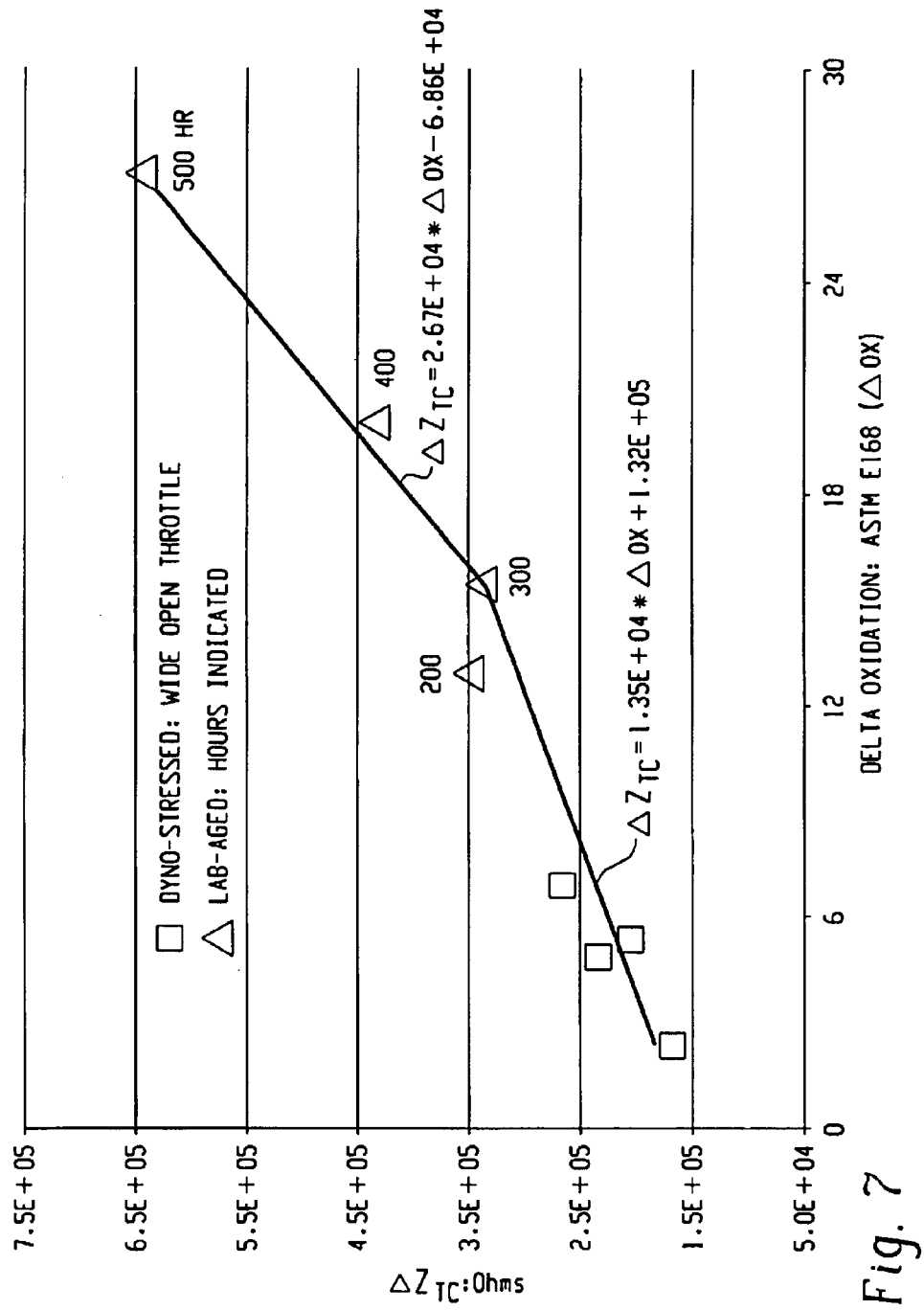
FIG. 7 is a graph similar to FIG. 6 plotting values of differential impedance as a function of ΔOX.

If the system answers in the negative at step 210, the system proceeds to step 214 and determines $\Delta OX$ from a lookup table of values of $\Delta OX$ versus $\Delta Z_{TC}$ based on the graph of FIG. 7 using the algorithm:

$$\Delta Z_{TC} = 2.67E+04 * \Delta OX - 6.86E+04.$$

After completing one of the operations 214, 212, the system proceeds to step 216 and stores the result as $\Delta OX_1$ and proceeds to execute a time delay of not less than about one hour at step 218. The system then proceeds to repeat steps 180 through 214 at step 220 and stores the result as $\Delta OX_2$ at step 224.

The system then proceeds to step 226 and computes the difference $\psi$ of the values of $\Delta OX$ by subtracting $\Delta OX_1$ from $\Delta OX_2$ and dividing the result by $\Delta T$. The system then proceeds to step 228 and recalls a stored value of $\Delta OX_{EOL}$ and proceeds to step 230 to compute the remaining useful life (RUL) by subtracting $\Delta OX_{EOL}$ from $\Delta OX_2$ and dividing the result by the computed value of $\psi$ and proceeds to step 232 to display the value of RUL.

Irrespective of which of TAN, $\Delta OX$ or MIN is calculated, if $\Delta Z_{TC}$ is measured equal or greater than $6.5\times10^5$, the ATF fluid is deemed to have reached the end of its useful life.

Although the invention has hereinabove been described with respect to the illustrated embodiments, it will be understood that the invention is capable of modification and variation and is limited only by the following claims.

What is claimed is:

1. A method of monitoring the condition of the fluid in an automatic transmission in real time comprising:

(a) disposing a pair of spaced electrodes in the fluid in the transmission;

(b) exciting one of said electrodes sequentially with a first relatively low frequency alternating voltage for measuring the effect of electrochemical interaction at the electrode surface through impedance variation and at a second relatively high frequency alternating voltage for measuring the effect of bulk fluid impedance;

(c) measuring the current in the other of said electrodes at said first and second frequencies and computing the difference in impedance $\Delta Z$ at said frequencies; and determining the temperature corrected value of the impedance difference $\Delta Z_{TC}$ from a known relationship of $\Delta Z$ as a function of temperature;

(d) determining a parameter selected from the group consisting of (i) ASTM D-664 TAN (ii) ASTM E168 Oxidation and (iii) ASTM D-5483 HPDSC Induction time from a lookup table of values of $\Delta Z_{TC}$ as a function of one of (i), (ii) and (iii); and, (e) providing an end of life (EOL) indication for the fluid when one of said TAN, Oxidation and HPDSC time reaches a predetermined limit.

2. The method defined in claim 1, wherein said step of disposing a pair of electrodes includes disposing a pair of concentric cylinders.

3. The method defined in claim 2, wherein said step of providing a pair of electrodes includes providing a pair of concentric cylindrical electrodes having a radial spacing of about 0.15 mm and an inner electrode diameter of about 6 mm and a length of about 38 mm and said step of providing an EOL indication includes providing an indication when $\Delta Z_{TC} \geqq 6.5 \times 10^5$ Ohms.

4. The method defined in claim 1, wherein said step of exciting one of said electrodes includes exciting at a first frequency not higher than 100 milliHertz (0.100 Hz) and exciting at a second frequency not less than 10 Hertz.

5. The method defined in claim 1, wherein said step of computing the difference in impedance includes computing the difference in the absolute values of the impedances.

6. The method defined in claim 1, wherein said step of computing the impedance difference includes computing the reactance from the phase shift angle of the current measured at said first and second frequencies.

7. The method defined in claim 1, wherein said step of providing an EOL includes providing an electrical signal proportional to $\Delta Z_{TC}$.

8. A method of monitoring the condition of the solvent dewaxed heavy paraffinic oil based fluid in an automatic transmission in real time comprising:

(a) disposing a pair of spaced electrodes in the fluid in the transmission;

(b) exciting one of said electrodes sequentially with a first relatively low frequency alternating voltage for measuring the effect of electrochemical interaction at the electrode surface through impedance variation and at a second relatively high frequency alternating voltage for measuring the effect of bulk fluid impedance;

(c) measuring the current in the other of said electrodes at said first and second frequencies and computing the difference in impedance $\Delta Z$ at said frequencies; and determining the temperature corrected value of the impedance difference $\Delta Z_{TC}$ from a known relationship of $\Delta Z$ as a function of temperature;

(d) determining a parameter selected from the group consisting of (i) ASTM D-664 TAN (ii) ASTM E168 Oxidation and (iii) ASTM D-5483 HPDSC Induction time from a lookup table of values of $\Delta Z_{TC}$ as a function of one of (i), (ii) and (iii); and, (e) providing an end of life (EOL) indication for the fluid when one of the conditions said TAN$\geqq$3.5, Oxidation$\geqq$30 and HPDSC<7.5 minutes occurs.

9. The method defined in claim 8, wherein said step of disposing a pair of electrodes includes radially spacing a first and second tubular member in concentric arrangement.

10. The method defined in claim 9, wherein said step of radially spacing includes spacing said first and second electrode about 0.15 mm.

* * * * *